United States Patent [19]

Seagraves

[11] Patent Number: 5,113,016
[45] Date of Patent: May 12, 1992

[54] MANUFACTURE OF PHTHALOYL CHLORIDES

[75] Inventor: Robert L. Seagraves, Pennsville, N.J.

[73] Assignee: E. I. Du Pont de Nemours and Company, Wilmington, Del.

[21] Appl. No.: 570,311

[22] Filed: Aug. 20, 1990

Related U.S. Application Data

[63] Continuation-in-part of Ser. No. 80,501, Jul. 31, 1987, abandoned.

[51] Int. Cl.$^5$ ..................... C07C 51/60; C07C 51/083
[52] U.S. Cl. .................................. 562/856; 562/888; 562/889; 562/897
[58] Field of Search ................. 562/856, 888, 889, 897

[56] References Cited

U.S. PATENT DOCUMENTS

| | | | |
|---|---|---|---|
| 2,367,501 | 1/1945 | Hull et al. | 260/546 |
| 2,575,159 | 11/1951 | Chassaing et al. | 260/546 |

*Primary Examiner*—Paul J. Killos
*Assistant Examiner*—Porfirio Nazario

[57] ABSTRACT

Excess terephthalic acid or isophthalic acid is reacted with a phosgene/DMF complex nearly to completion in one or more stages to form terephthaloyl chloride or isophthaloyl chloride; in another stage, by-product formylbenzoyl chloride is oxidized and terephthaloyl chloride or isophthaloyl chloride containing less than 100 ppm of formylbenzoyl chloride and/or dichlorotoluoylchloride is recovered.

24 Claims, No Drawings

MANUFACTURE OF PHTHALOYL CHLORIDES

CROSS-REFERENCE TO PRIOR APPLICATION

This application is a continuation-in-part of application Ser. No. 07/080,501 filed 31 Jul. 1987.

FIELD OF THE INVENTION

The present invention relates to a process for manufacturing terephthaloyl chloride (TCl) and isophthaloyl chloride (ICl) having reduced content of color-formers.

BACKGROUND OF THE INVENTION

TCl and ICl each have been synthesized in continuous or batch processes which involve the reaction of phosgene with terephthalic acid (TPA) or isophthalic acid (IPA) in the presence of an equimolar complex of phosgene and dimethylformamide (DMF). Parker et al. in U.S. Pat. No. 3,184,506 disclosed that it is necessary in a continuous process to maintain some unreacted TPA or IPA in the reaction zone and the product stream; otherwise, the DMF/phosgene complex that catalyzes the phosgenation reaction will degrade. TPA and IPA can be manufactured by the oxidation of p-xylene and m-xylene respectively. Those reactions results in the production respectively of 4-carboxybenzaldehyde and 3-carboxybenzaldehyde (collectively CBA) as intermediates. Because of incomplete oxidation of those intermediates, 4-carboxybenzaldehyde and 3-carboxybenzaldehyde, respectively, are found in the TPA and IPA so-produced in amounts generally in the range between about 200 and 2000 ppm. When CBA-containing TPA or CBA-containing IPA is reacted with the DMF/phosgene complex, CBA is converted, respectively, to 4-formylbenzoyl chloride or 3-formylbenzoyl chloride (collectively FBC). Reaction of FBC with the DMF/phosgene complex gives alpha,alpha-dichloro-4-toluoyl chloride or alpha,alpha-dichloro-3-toluoyl chloride (collectively DCTC).

In accordance with the present invention, it has been found that even when present in small quantities, both FBC and DCTC cause unwanted color formation when either TCl or ICl containing the same is used to form a polymer. Such coloration is frequently unacceptable, particularly in respect of high performance engineering plastics, e.g. polyphenolate/carbonate. So as to avoid color formation in such polymers, the polymer manufacturer may require TCl or ICl having less than 100 ppm, preferably less than 50 ppm of FBC and/or DCTC.

Neither the process for oxidizing p-xylene nor that for oxidizing m-xylene can be operated economically to produce TPA or IPA having a CBA content of 100 ppm or less. One or more steps must be added to the process for manufacturing TPA or IPA so as to purify the acid. For example, IPA has been crystallized from acetic acid, a costly corrosive process. High purity TPA has been produced by catalytically reducing CBA to p-toluic acid and removing the latter by crystallization, also at added cost. Removal of FBC and DCTC from TCl or ICl by crystallization and/or distillation are costly undertakings requiring substantial investment, particularly for solvent recovery facilities. Furthermore, the prior art has failed to provide a procedure whereby TPA or IPA can be reacted with the DMF/phosgene complex so as to produce TCl or ICl having less than 100 ppm of FBC and/or DCTC. Conversion of CBA in the reaction with the phosgene/DMF complex is essentially quantitative. Consequently, when operating in accordance with the prior art, the aggregate amounts of FBC and DCTC found in the TCl or ICl will be directly proportional to the amount of CBA found in the TPA or IPA starting material.

BRIEF SUMMARY OF THE INVENTION

The present invention relates to a process for synthesizing TCl and ICl from TPA and IPA, respectively, which provides a final product containing less than about 100 ppm of FBC and/or DCTC. The process of this invention achieves that result without resorting to the prior art procedures, thus avoiding the considerable expense associated with them.

DETAILED DESCRIPTION OF THE INVENTION

It has been now been discovered that the phosgene/DMF complex reacts with CBA at a faster rate than with either TPA, IPA or FBC. It has also now been discovered that while FBC is formed rapidly by the reaction of CBA and the phosgene/DMF complex, very little FBC is converted to DCTC until the reaction of TPA or IPA with the phosgene/DMF complex reaches substantial completion; i.e., so long as some TPA or IPA remains unreacted. Based on those discoveries, in the process of the present invention, (a) TPA or IPA in excess of the stoichiometric amount is reacted with the phosgene/DMF complex in one or more stages to less than completion (i.e. so that the reaction to form ICl or TCl very nearly approaches but never quite reaches completion), and (b) in another stage, the FBC content of the reaction mass is oxidized in the presence of TCl or ICl to a high boiling material that can be separated from the final product simply and inexpensively, and (c) recovering TCl or ICl containing, respectively, less than about 100 ppm of FBC and/or DCTC, preferably less than about 50 ppm of FBC and/or DCTC. Air is the preferred oxidizing agent, but others could be used, e.g., ozone, $H_2O_2$, benzoyl peroxide (any one other than air or ozone can cause yield loss).

One embodiment of the invention comprises a continuous process having three stages. In the first stage, TPA or IPA, phosgene and DMF are fed continuously to a first reaction vessel which contains a solvent for the TPA or IPA. The DMF and a portion of the phosgene combine in situ to form the phosgene/DMF complex described above, and the so-formed complex reacts with TPA or IPA to form TCl or ICl. A slurry of a substantial excess of TPA or IPA in TCl or ICl continuously exits the first reaction vessel along with DMF, and is continuously transferred to a second reaction vessel (second stage of process) to which phosgene is fed continuously. A slurry of a slight excess of TPA in TCl or IPA in ICl continuously exits the second reaction vessel and is transferred to a third reaction vessel (third stage) in which FBC is oxidized to 4-carboxybenzoyl chloride or 3-carboxybenzoyl chloride which reacts with the TCl or ICl to form a high boiling anhydride. When 3-formylbenzoyl chloride is oxidized, the resulting high boiling anhydride can be represented by the formula:

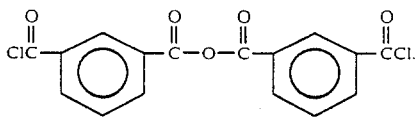

When 4-formylbenzoyl chloride is oxidized, the resulting high boiling anhydride can be represented by the formula:

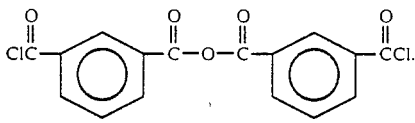

In the first stage (reaction vessel) of the above-described 3-stage continuous process, one reacts to less than completion TPA or IPA in substantial excess of the stoichiometric amount with the phosgene/DMF complex to form, respectively, TCl or ICl. Having the faster reaction rate, the CBA reacts with the phosgene/DMF complex to form FBC irrespective of the amount of TPA or IPA present. However, FBC apparently can not compete for reaction with the phosgene/DMF complex so long as a substantial excess of TPA or IPA is present. As a consequence, a more or less constant amount of FBC, with little or no DCTC, will be observed in the first stage so long as an adequate excess of TPA or IPA is present. Moreover, the presence of excess TPA or IPA also avoids degradation of the DMF/phosgene complex that catalyzes the reaction of TPA or IPA with phosgene. In the second stage of the process, one effects substantial completion of the reaction with TPA or IPA in slight excess of the stoichiometric amount needed to react with all of the phosgene available in the combined first and second stages. Substantial completion can be determined by analyzing for TPA or IPA. In the third stage of the process, FBC is oxidized so as to form the above-described high boiling anhydride which can be separated from the TCl or ICl final product by a simple inexpensive distillation procedure.

The exact amounts of excess TPA or IPA that are used in the first two stages of the continuous process can be determined experimentally, e.g. by observing the amount of DCTC present in the TCl or ICl formed in each of those two stages. In the first stage, there will be very little if any DCTC formed so long as there is a substantial excess of TPA or IPA present. So long as TPA or IPA is present in slight excess, there will be very little more DCTC formed in the second stage than in the first stage. It will be understood that there may be a small amount of unreacted phosgene in the system which will not be taken into account in determining any such excess. If the DCTC content starts to increase in the first stage, more TPA or IPA or less phosgene should be fed to the reaction vessel. If the DCTC content starts to increase in the second stage of continuous process, the phosgene feed should be reduced. Usually the amount of excess acid used in the first stage of the continuous process is such that the product at the end of that stage contains between about 3 and 15 weight % of TPA or IPA in excess of the stoichiometric amount needed for completion of the reaction with phosgene, preferably in the range between about 6 and 10 weight %. On the other hand, TPA or IPA is usually used in the second stage of the continuous process in an amount such that about 0.2 to about 2.5% TPA or IPA remains in the product after the reaction of TPA or IPA with the DMF/phosgene complex reaches substantial completion, preferably between about 0.2 and 1.0 weight percent. In order to reach any of those levels of TPA or IPA in the second stage of the continuous process, one can either control the TPA or IPA output from the first stage or the phosgene input to the second stage of the process, with the latter being preferred because it is easier to control. Reaction temperatures can also be determined experimentally. Generally, in the first stage of the continuous process the temperature should be between about 80 and 120 degrees C, preferably between about 90 and 105 degrees C. A higher reaction temperature can be used in the second stage than in the first stage; i.e. between about 80° and 140° C., preferably between about 110° and 130° C. The temperature for the oxidation reaction (the third stage of the continuous process) should be between about 185 and 240 degrees C, preferably between about 195 and 205 degrees C.

In another embodiment, the process is run in a batch fashion. In that embodiment, the total amount of TPA or IPA to be reacted plus the DMF for the DMF/phosgene complex are charged to the reaction vessel along with a solvent for the acid. Phosgene is thereafter metered into the vessel until only a slight excess of TPA or IPA remains; e.g. that described above for the second stage of the continuous process of this invention. Thereafter, FBC present in the product TCl or ICl is oxidized to the high boiling anhydride described above. Bach process conditions can be determined experimentally just as in the continuous process. For example, temperatures in that part of the batch process in which ICl or TCl is prepared from IPA or TPA should be between about 80 and 120 degrees C, preferably between about 90 and 100 degrees C. The oxidation reaction temperature should be in the range between about 185 and 240 degrees C, preferably between about 195 and 205 degrees C.

In yet another embodiment of the process of the invention, TPA or IPA is separated from TCl or ICl while the former is still present in excess. That excess may comprise that of either the first or second stage of the continuous process described, preferably the former. Following separation of excess TPA or IPA, FBC is oxidized as described above. The process of this latter embodiment of the invention may be carried out in either a batch or continuous manner, preferably the latter. Other reaction conditions will track those described above.

In any of the above-described embodiments, the solvent of choice is the TCl or ICl to be prepared as the end product. But other organic liquids can be used instead, e.g. toluene, hexane, heptane, octane, benzene, chlorobenzene, dichlorobenzene or the like. If a solvent other than TCl or ICl is, enough of it must be removed so as to be able to reach oxidation temperature. In any event, TPA and IPA are not readily soluble in any of the foregoing solvents, and as a consequence only a part of the TPA of IPA used in any of the foregoing embodiments will be in solution.

In all of the embodiments of this invention, it is important that the particle size of TPA be in the range between that of flour and sand. Generally it will be below about 100 microns, preferably below about 75 microns. Otherwise, it reacts too slowly and execessive amounts of DCTC are formed. No such problem has been observed with IPA.

The following Examples are given in further illustration of the invention but not by way of limitation. Unless specified otherwise, percentages are given by weight, and temperatures are in degrees C.

EXAMPLE 1

(Best Mode)

The first stage of the equipment used in conducting the continuous process was a countercurrent, multistage sieve tray reactor with temperature and pressure-measuring means and having a liquid recycle stream composed of IPA reactant, ICl product, HCl, $CO_2$ and DMF.HCl. The recycle stream passed through a heat exchanger to maintain temperature. DMF and IPA were mixed with the recycle stream just before it returned to the top of the reactor. Phosgene was fed through multiple spargers near the bottom of the reactor. Agitation was provided by the passage of gases through the reactor (phosgene, hydrogen chloride and carbon dioxide). The reactor was vented to a scrubber to remove hydrogen chloride and small amounts of phosgene. A portion of the recycle stream was fed to the second stage in order to maintain a constant volume in the first stage. The second stage was a single stage reactor with recycle from top to bottom. Effluent from the first stage and phosgene were fed into the bottom of the reactor. Temperature and pressure were monitored but not controlled. Any unreacted phosgene from the second stage was vented back to the first stage for further reaction. A portion of the second stage recycle stream was fed to the third stage in order to maintain a constant volume in the second stage. The third stage was a tank with external recycle stream that passed through a heat exchanger to control third stage temperature. Temperature and pressure were monitored. Air was sparged directly into the liquid reaction mass in the third stage. The third stage was vented to a scrubber to remove hydrogen chloride. A portion of the third stage recycle stream was fed to a simple distillation train to maintain a constant volume in the third stage.

The foregoing equipment was used to prepare ICl over a 16-hour period using the following materials under the following conditions:

|  | Pounds/Hour | Pound Mols |
| --- | --- | --- |
| First Stage |  |  |
| Phosgene Feed: | 9071 | 91.63 |
| IPA Feed: | 8700 | 52.41 |
| (IPA contained about 200 ppm CBA & 7.6% of IPA was insoluble) |  |  |
| DMF Feed: | 25 | 0.36 |
| Temperature: |  |  |
| Top of reactor: 91° C. |  |  |
| Bottom of reactor: 99° C. |  |  |
| Pressure: |  |  |
| Bottom of reactor: 10 psig |  |  |
| FBC: 225 ppm |  |  |
| DCTC: Non-detectable |  |  |
| Second Stage |  |  |
| Phosgene Feed: | 1410 | 14.24 |
| Temperature: 117° C. |  |  |
| Pressure: 17 psig |  |  |
| Insoluble IPA: 0.25-0.50% |  |  |
| FBC: 180 ppm |  |  |
| DCTC: 40 ppm |  |  |
| Third Stage |  |  |
| Pressure: 24.5 psig |  |  |

-continued

|  | Pounds/Hour | Pound Mols |
| --- | --- | --- |
| Temperature: 197° C. |  |  |
| FBC: Non-detectable |  |  |
| DCTC: 40 ppm |  |  |
| Air Feed: 1200 SCF/Hr. |  |  |
| (Non-detectable ≦ 30 ppm) |  |  |

EXAMPLE 2

(Batch)

In a one liter, four neck, round bottom, creased flask, equipped with agitator, thermometer, gas inlet tube which extends below the liquid level, heater and condenser connected to a phosgene scrubber, were charged:

| 550 g | isophthaloyl chloride |
| --- | --- |
| 55 g | isophthalic acid |
| 0.22 g | 3-carboxybenzaldehyde |
| 2.0 cc | dimethylformamide. |

The slurry was heated to 90° C. Phosgene was added into the reaction mixture at 200 cc/min. The reaction mass was agitated and heated rapidly to 105° C. and held until the reaction was complete. Samples were taken for gas chromatographic analysis for FBC and DCTC. When the reaction of IPA reached completion, a color change was noted and insoluble isophthalic acid was no longer visible. The analysis shown below indicate that FBC forms rapidly and is not converted to DCTC until almost all of the isophthalic acid has been consumed.

| Time, min. | FBC, ppm | DCTC, ppm | Color |
| --- | --- | --- | --- |
| 15 | 370 | ND | Light yellow |
| 75 | 440 | ND | Light yellow |
| 120 | 440 | ND | Light yellow |
| 240 | 400 | ND | Light yellow |
| 270 | 400 | ND | Light yellow |
| 315 | 100 | Trace | Yellow** |
| 330 | Trace | 190 | Dark yellow |
| 345 | ND | 240 | Light brown |
| 360 | ND | 240 | Brown |

ND — not detectable.
**No insoluble IPA visible.

What is claimed is:

1. A process for preparing phthaloyl chlorides having reduced content of formylbenzoyl chlorides and dichlorotoluoyl chlorides which comprises (a) reacting to less than completion terephthalic acid or isophthalic acid in excess of the stoichiometric amount with phosgene/dimethylformamide complex at a temperature in the range between about 80° and about 120° C. to form, respectively, terephthaloyl chloride or isophthaloyl chloride;

(b) in the presence of terephthaloyl chloride or isophthaloylchloride and at a temperature in the rand between about 180° and about 240° C., oxidizing by-product 4-formylbenzoyl chloride or 3-formylbenzoyl chloride to an anhydride which can be represented, respectively, by the formula:

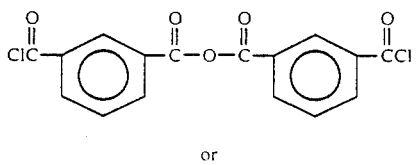

or

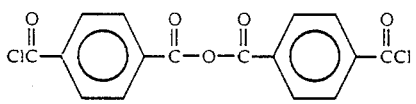

and (c) recovering as a final product terephthaloyl chloride or isophthaloyl chloride containing respectively less than about 100 pppm of either (i) 4-formylbenzoyl chloride, 3-formylbenzoyl chloride, alpha,alpha-dichloro-4-toluoyl chloride, or alpha,alpha-dichloro-3-toluoyl chloride, or (ii) a mixture of 4-formylbenzoyl chloride and alpha,alpha-dichloro-4-toluoyl chloride, or (iii) a mixture of 3-formylbenzoyl chloride and alpha,alpha-dichloro-3-toluoyl chloride.

2. The process of claim 1 wherein said excess is in the range between about 0.2 and 2.5 weight percent.

3. The process of claim 2 wherein said excess is in the range between about 0.2 and 1.0 weight percent.

4. The process of claim 1 wherein said terephthalic acid has a particle size of less than about 100 microns.

5. The process of claim 4 wherein said particle size is less than about 75 microns.

6. The process of claim 1 wherein said final product contains less than 50 ppm of either (i) 4-formylbenzoyl chloride, 3-formylbenzoyl chloride, alpha,alpha-dichloro-4-toluoyl chloride, or alpha,alpha-dichloro-3-toluoyl chloride, or (ii) a mixture of 4-formylbenzoyl chloride and alpha,alpha-dichloro-4-toluoyl chloride, or (iii) a mixture of 3-formylbenzoyl chloride and alpha,alpha-dichloro-3-toluoyl chloride.

7. The process of claim 6 wherein said excess is in the range between about 0.2 and 2.5 weight percent.

8. The process of claim 7 wherein said excess is in the range between about 0.2 and 1.0 weight percent.

9. The process of claim 6 wherein said terephthalic acid has a particle size of less than about 100 microns.

10. The process of claim 9 wherein said particle size is less than about 75 microns.

11. A process for preparing phthaloyl chlorides having reduced content of formylbenzoyl chlorides and dichlorotoluoyl chlorides which comprises
    (a) reacting to less than completion terephthalic acid or isophthalic acid in substantial excess of the stoichiometric amount with the phosgene/DMF complex at a temperature in the range between about 80° and about 120° C. to form, respectively, terephthaloyl chloride or isophthaloyl chloride;
    (b) effecting substantial completion of the said reaction with terephthalic acid or isophthalic acid in slight excess of the stoichiometric amount at a temperature in the range between about 80° and about 140° C.;
    (c) in the presence of terephthaloyl or isophthaloyl chloride, oxidizing by-product 4-formylbenzoyl chloride or 3-formylbenzoyl chloride at a temperature in the range between about 180° and about 240° C. to an anhydride which can be represented respectively by the formula:

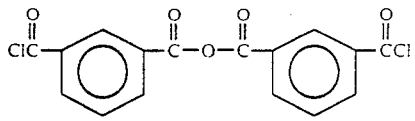

or

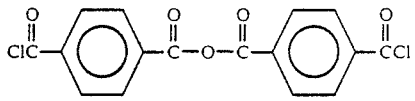

and (d) recovering terephthaloyl chloride or isophthaloyl chloride containing respectively less than about 100 ppm or either (i) 4-formylbenzoyl chloride, 3-formylbenzoyl chloride, alpha,alpha-dichloro-4-toluoyl chloride, or alpha,alpha-dichloro-3-toluoyl chloride, or (ii) a mixture of 4-formylbenzoyl chloride and alpha,alpha-dichloro-4-toluoyl chloride, or (iii) a mixture of 3-formylbenzoyl chloride and alpha,alpha-dichloro-3-toluoyl chloride.

12. The process of claim 11 wherein said substantial excess is in the range between about 3.0 and 15 weight percent.

13. The process of claim 12 wherein said excess is in the range between about 6 and 10 weight percent.

14. The process of claim 11 wherein said slight excess is in the range between about 0.2 and 2.5 weight percent.

15. The process of claim 14 wherein said excess is in the range between about 0.2 and 1.0 weight percent.

16. The process of claim 11 wherein said terephthalic acid has a particle size of less than about 100 microns.

17. The process of claim 16 wherein said particle size is less than about 75 microns.

18. The process of claim 11 wherein said final product contains less than 50 ppm of either (i) 4-formylbenzoyl chloride, 3-formylbenzoyl chloride, alpha,alpha-dichloro-4-toluoyl chloride, or alpha,alpha-dichloro-3-toluoyl chloride, or (ii) a mixture of 4-formylbenzoyl chloride and alpha,alpha-dichloro-4-toluoyl chloride, or (iii) a mixture of 3-formylbenzoyl chloride and alpha,alpha-dichloro-3-toluoyl chloride.

19. The process of claim 18 wherein said substantial excess is in the range between about 3.0 weight and 15 weight percent.

20. The process of claim 19 wherein said excess is in the range between about 6 and 10 weight percent.

21. The process of claim 18 wherein said slight excess is in the range between about 0.2 and 2.5 weight percent.

22. The process of claim 21 wherein said excess is in the range between about 0.2 and 1.0 weight percent.

23. The process of claim 18 wherein said terephthalic acid has a particle size of less than about 100 microns.

24. The process of claim 23 wherein said particle size is less than about 75 microns.

* * * * *